United States Patent [19]

Gatto

[11] Patent Number: 4,877,902

[45] Date of Patent: Oct. 31, 1989

[54] POLYTHIOBISPHENOL PROCESS

[75] Inventor: Vincent J. Gatto, Baton Rouge, La.

[73] Assignee: Ethyl Corporation, Richmond, Va.

[21] Appl. No.: 167,876

[22] Filed: Mar. 14, 1988

[51] Int. Cl.$^4$ ............................................. C07C 148/02
[52] U.S. Cl. ..................................................... 568/23
[58] Field of Search ........................................... 568/23

[56] References Cited

U.S. PATENT DOCUMENTS

| | | | |
|---|---|---|---|
| 3,060,121 | 10/1962 | Orloff et al. | 568/23 |
| 3,129,213 | 4/1964 | Worrel | 568/23 |
| 3,145,176 | 8/1964 | Knapp et al. | 524/139 |
| 3,479,407 | 11/1969 | Laufer | 568/23 |
| 3,718,699 | 2/1973 | Fujisawa et al. | 568/23 |
| 3,812,192 | 5/1974 | Gabler et al. | 568/23 |
| 4,740,578 | 4/1988 | Onoe et al. | 568/23 |

FOREIGN PATENT DOCUMENTS 1290132  9/1972  United Kingdom .

*Primary Examiner*—Mary E. Ceperley
*Attorney, Agent, or Firm*—J. D. Odenweller

[57] ABSTRACT

Mixtures of 4,4′-dithiobis and 4,4′-trithiobis(2,6-dialkylphenols) are made by reacting a 2,6-dialkylphenol with $S_2Cl_2$ in a solvent comprising a nitroalkane, e.g. nitromethane, and optionally containing an acetonitrile co-solvent at a temperature of $-10°$ to $30°$ C.

20 Claims, No Drawings

POLYTHIOBISPHENOL PROCESS

BACKGROUND

Mono- and polythiobis dialkylphenols are useful as antioxidants in a broad range of substrates such as lubricating oil and polymers (Knapp, U. S. 3,145,176). They have been made in non-polar solvents such as benzene, toluene, hexane and the like. These methods however produce an oily product containing significant quantities of starting material and impurities while purer products are obtained using the later methods. The reactions must be carried out at relatively cold temperatures (−20° to −40° C.). This makes the process less economical. They have also been made in acetonitrile (Tamatsu et al. U.S. Pat. No. 3,718,699) using an iron or ferric chloride catalyst. British No. 1,290,132 report that with 2,6-di-tert-butylphenol and $S_2Cl_2$, Virtually no reaction takes place at room temperature unless the reaction is continued for over 6 hours. British No. 1,290,132 requires the use of a Lewis acid to cause the reaction to proceed in a solvent such as hexane, carbon tetrachloride, toluene, benzene, chlorobenzene, methanol, diethylether or glacial acetic acid.

SUMMARY

According to the present invention a process is provided which produces mainly dithiobis and trithiobis-dialkylphenol at or slightly below ambient temperature in high yield and as a solid which readily precipitates from the reaction mixture and can be recovered by filtration. No catalyst is required. Such a process is more economical, from a commercial standpoint, than prior methods which require substantial cooling and extensive purification.

DESCRIPTION OF THE PREFERRED EMBODIMENTS

A preferred embodiment of the invention is a process for making 4,4'-polythiobis(2,6-dialkylphenols) said process comprising reacting a 2,6-dialkylphenol with $S_2Cl_2$ in a nitroalkane solvent at −10° to 30° C. to form a mixture of mainly 4,4'-dithiobis and 4,4'-trithiobis(2,6-dialkylphenol).

The process can be readily carried out by placing the 2,6-dialkylphenol and solvent in a stirred reaction vessel and adding $S_2Cl_2$ either neat or with additional solvent to the stirred reaction mixture held at reaction temperature. Preferably an inert gas such as nitrogen is bubbled through the mixture to assist in removal of evolved HCl. The product precipitates as a solid and may be recovered by filtration.

Any 2,6-dialkylphenol capable of forming a polythiobisphenol can be used. The alkyl substituents can contain 1–12 or more carbon atoms such as methyl, ethyl, isopropyl, n-propyl, sec-butyl, isobutyl, tert-butyl, sec-hexyl, tert-octyl, secdodecyl, 2-ethylhexyl and the like. Cycloalkyls containing about 5–8 carbon atoms can also be present such as cyclopentyl, cyclohexyl, cyclooctyl and the like. Likewise aryl-substituted alkyl groups may be present such as benzyl, α-methylbenzyl, α,α-dimethylbenzyl and the like.

Representative examples of 2,6-di-alylphenols that can be used in the process are 2,6-di-tert-butylphenol, 2-methyl-6- tert-butylphenol, 2-methyl-6-tert-pentyl-phenol, 2,6-di-isopropylphenol, 2,6-di-sec-butylphenol, 2-methyl-6-sec-dodecylphenol, 2,6-dipentylphenol, 2,6-di-hexylphenol, 2-methyl-6cyclo-octylphenol, 2-tert-butyl-6-benzylphenol, 2,6-di(α-methylbenzyl)phenol, 2-tert-butyl-6(α,α-methylbenzyl)phenol, 2,6-di(α,α-dimethylbenzyl)phenol, 2-methyl-6(α,α-dimethylbenzyl)phenol and the like.

The preferred 2,6-dialkylphenols are those in which at least one alkyl is tert-alkyl containing 4–12 carbon atoms. More preferably both alkyls are tert-alkyls. The most preferred 2,6-dialkylphenol is 2,6-di-tert-butylphenol.

Nitroalkane solvents include any normally liquid nitroalkane. A few examples are nitromethane, nitroethane, 1-nitropropane, 2-nitropropane, 1-nitrobutane, 1-nitro-2-methylpropane, nitrocyclohexane and the like. The lower nitroalkanes such as nitromethane and nitroethane are preferred, especially nitromethane.

The amount of nitroalkane should be a solvent amount. That is, an amount that will dissolve the reactants under reaction conditions. Preferably the amount is also limited to an amount that will cause precipitation of a substantial portion of the product when the reaction mixture is cooled at the end of the reaction period. A useful range of nitroalkane solvent is about 100–500 parts by weight per mole part of starting phenol. A more preferred amount of nitroalkane solvent is about 100–300 parts by weight per mole part of dialkylphenol. A preferred amount of nitroalkane solvent is 150–300 parts by weight per mole part of dialkylphenol.

In a further preferred embodiment, an acetonitrile cosolvent is used in combination with the nitroalkane solvent. The amount of acetonitrile can vary from 0–500 parts by weight per mole part of dialkylphenol. A preferred amount of acetonitrile co-solvent is about 50–250 parts and still more preferably 100–200 parts by weight per mole part of 2,6-dialkylphenol.

The preferred solvent combination is 150–300 parts of nitromethane and 100–200 parts of acetonitrile per mole part of dialkylphenol. A more preferred solvent combination is about 180–200 parts of nitromethane and 100–130 parts of acetonitrile per mole part of dialkylphenol. All parts are by weight.

It is preferred to use dry solvents to minimize hydrolysis of the $S_2Cl_2$. The solvents need not be bone-dry but the water content is preferably below 0.1 weight percent and more preferably below 0.05 weight percent.

The process is conducted at temperatures near or slightly below ambient. A useful temperature range is about −10° to +30° C. A more preferred temperature range is −10° to +15° C. A most preferred temperature range is −0° C. to +10° C.

The amount of $S_2Cl_2$ is about 0.40–0.75 moles per mole of dialkylphenol. A preferred range is about 0.40–0.60 moles and most preferably 0.45 to 0.55 moles per mole of dialkylphenol. Although not necessary, the $S_2Cl_2$ can be pre-mixed with a portion of the solvent used in the process and added to the reaction mixture as a solution.

The time required to carry out the reaction is not a completely independent variable and depends on a number of factors such as reaction scale. A useful reaction period is about 1–12 hours. A more general reaction time is about 4–8 hours.

The following examples show how the process is carried out and the results that are achieved.

EXAMPLE 1

This example shows the results obtained using only acetonitrile as the solvent under about the same reaction conditions as used in subsequent examples. This example is included for comparative purposes.

A glass reaction vessel was charged with 88.5 grams (0.43 moles) of 2,6-di-tert-butylphenol and 211 ml of acetonitrile cooled to 0° C. While stirring, 30.4 grams (0.225 moles) of $S_2Cl_2$ was added dropwise at 0–3° C. over a one-hour period. The reaction was stirred one hour at 3° C. The solids were removed by filtration and washed with cold (5° C.) acetonitrile to yield 32.9 grams of wet yellow solids. The solids were dried under vacuum at room temperature to give 32.8 grams of product (mp 130–144° C.). The yellow solid was analyzed by high pressure liquid chromatography (HPLC) to give the following results:

|              | Weight Percent |
|--------------|----------------|
| monothiobis  | 0.22           |
| dithiobis    | 92.5           |
| trithiobis   | 2.6            |
| tetrathiobis | 0.91           |

The yield of 4,4'-di-thiobis(2,6-di-tert-butylphenol) was 32.0%.

EXAMPLE 2

In a glass reaction vessel was placed 206.4 grams (1.0 mole) of 2,6-di-tert-butylphenol, 117.9 grams of acetonitrile and 198.3 grams of nitromethane. The mixture was stirred to form a solution and cooled to 0° C. Then 69.6 grams (0.5 moles) of $S_2Cl_2$ was added over a 3-hour period at 0°–5° C. while stirring and passing nitrogen through the reaction mixture to remove evolved HCl. The nitrogen-HCl vent was passed to a caustic scrubber. The reaction mixture was then allowed to warm to 20° C. over 30 minutes and nitrogen purge was continued until HCl content of the reaction mixture dropped to 0.3 weight percent. The mixture was then cooled to 5° C. and the solids isolated by filtration. The solids were washed with a 40/60 acetonitrile/nitromethane mixture. The solids were dried leaving 192.7 grams of a product having a mp of 103°–140° C. The yellow solids were analyzed by high pressure liquid chromatrograph (HPLC) to give the following results:

|              | Weight Percent |
|--------------|----------------|
| monothiobis  | 0.22           |
| dithiobis    | 73.1           |
| trithiobis   | 25.1           |
| tetrathiobis | None Detected  |

The yield of solids containing mostly dithiobis and trithiobis product was 80.5%.

EXAMPLE 3

In a glass reaction flask was placed 51.6 grams of 2,6-di-tert-butylphenol (0.25 moles) and 82.6 grams of nitromethane. In an addition funnel was placed 49.1 grams of acetonitrile and 18.2 grams (0.131 moles) of $S_2Cl_2$. The $S_2Cl_2$ solution was added to the stirred reaction mixture at 0°–3° C. over 1.5 hours. The mixture was stirred an additional hour at 0°–3° C. and then filtered at 0°–3° C. to recover a fine solid product. This product was washed with 20 grams of cold (3° C. acetonitrile) to give 51.3 grams of wet product. The product was dried under vacuum (0.1 mm) at room temperature for 2 hours to a dry weight of 46.8 grams. The solid was analyzed by HPLC as follows:

|              | Weight Percent |
|--------------|----------------|
| monothiobis  | 0.49           |
| dithiobis    | 57.5           |
| trithiobis   | 38.9           |
| tetrathiobis | 0.61           |
| pentathiobis | —              |

The mass yield of solids was 77.7%.

EXAMPLE 4

In a reaction flask was placed 58.9 grams of acetonitrile, 99.2 grams of nitromethane and 103.2 grams (0.5 moles) of 2,6-di-tert-butylphenol. To this was added 36.4 grams (0.26 moles) of $S_2Cl_2$ at 3° C. over 1.5 hours while stirring. Stirring was continued 1 hour at 3° C. and the mixture was filtered at 3° C. to recover a solid product which was washed with a cold (3° C.) 50/50 acetonitrile/nitromethane mixture.

The solids were dried under vacuum to give 101.2 grams of product (mp 99°–133° C.). The product analyzed by HPLC to give the following results.

|              | Weight Percent |
|--------------|----------------|
| monothiobis  | 0.52           |
| dithiobis    | 61.4           |
| trithiobis   | 34.8           |
| tetrathiobis | 0.63           |
| pentathiobis | —              |

The mass yield of solids containing dithiobis and trithiobis product was 83.8 percent.

EXAMPLE 5

In a reaction flask was placed 51.6 grams (0.25 moles) of 2,6-di-tert-butylphenol, 41 grams of nitromethane and 24.4 grams of acetonitrile. While stirring at 3° C., 16.3 grams (0.12 moles) of $S_2Cl_2$ was added dropwise over a 1.25 hour period. Stirring was continued 30 minutes at 3° C. and then the mixture was stirred 30 minutes at 25° C. The solids were filtered off and washed with 20 ml of 50/50 nitromethane/acetonitrile mixture. The solids were dried for 1 hour under vacuum to give 37.6 grams of product (mp 95°–142° C.). The solid was analyzed by HPLC with the following results:

|              | Weight Percent |
|--------------|----------------|
| monothiobis  | 0.68           |
| dithiobis    | 84.2           |
| trithiobis   | 10.8           |
| tetrathiobis | 0.33           |
| pentathiobis | —              |

The mass yield of solids containing dithiobis and trithiobis product was 63.4 percent.

EXAMPLE 6

In a glass reaction flask was placed 103.2 grams (0.5 moles) of 2,6-di-tert-butylphenol, 50 grams of nitroethane and 50 grams of acetonitrile. While stirring at 3° C., 34.8 grams (0.25 moles) of $S_2Cl_2$ was added dropwise over a 3.5 hour period. Stirring was continued 30 minutes at 3° C. while passing nitrogen through the reaction mixture to remove HCl. The reaction mixture was then allowed to warm to 22° C. over 30 minutes and the nitrogen purge was continued for 2 hours. The mixture was then cooled to 5° C. and the solids isolated by filtration. The solids were washed with acetonitrile and dried leaving 80.7 grams of a product having a mp of 103°–142° C. The yellow solids were analyzed by high pressure liquid chromatography (HPLC) to give the following results:

|  | Weight Percent |
| --- | --- |
| monothiobis | 0.43 |
| dithiobis | 81.2 |
| trithiobis | 13.4 |
| tetrathibis | 0.50 |

The mass yield of solids containing dithiobis and trithiobis product was 67.4 percent.

The following two examples were carried out near ambient temperature. They show the dramatic differences obtained in the product when a nitromethane/acetonitrile co-solvent system replaces a system containing only acetonitrile as solvent. Example 7 was run in acetonitrile and the product was isolated as an oil. Example 8 was run in acetonitrile/nitromethane and the product was predominantly a solid.

EXAMPLE 7

A glass reaction vessel was charged with 88.5 grams (0.43 moles) of 2,6-di-tert-butylphenol and 166 grams of acetonitrile. While stirring, 30.4 grams (0.225 moles) of S$_2$Cl$_2$ was added dropwise between 24°–26° C. over a one-hour period. The reaction was cooled to 3° C. and stirred for an additional hour at 3° C. No solids were formed. The homogenous reaction mixture was concentrated under vacuum at 90° C. to recover 103 grams of an oil. The oil was analyzed by high pressure liquid chromatography (HPLC) to give the following results:

|  | Weight Percent | |
| --- | --- | --- |
|  | Solids | Oil |
| monothiobis | — | 3.7 |
| dithiobis | — | 35.5 |
| trithiobis | — | 25.4 |
| tetrathiobis | — | 9.2 |

The yield of 4,4'-dithiobis(2,6-di-tert-butylphenol) was 35.8 percent.

EXAMPLE 8

A glass reaction Vessel was charged with 103.2 grams (0.5 moles) of 2,6-di-tert-butylphenol, 58.9 grams of acetonitrile and 99.2 grams of nitromethane. The mixture was stirred while 34.8 grams (0.25 moles) of S$_2$Cl$_2$ was added over a 3½ hour period at 20°–22° C. Dry nitrogen was passed through the reaction mixture to remove generated HCl. The mixture was stirred an additional hour at 20° C. and then stirred 40 minutes at 3° C. The resulting slurry was filtered at 3° C. and the solids washed with a 40/60 acetonitrile/nitromethane mixture. The solids were dried under vacuum leaving 75.2 grams of a product having a mp of 100°–142° C. High pressure liquid chromatography (HPLC) of the solids gave the following results:

|  | Weight Percent |
| --- | --- |
| monothiobis | 0.22 |
| dithiobis | 80.1 |
| trithiobis | 11.8 |
| tetrathiobis | 0.56 |

The mass yield of solids containing dithiobis and trithiobis products was 62.8 percent.

As shown by the above example the process carried out using the combination of nitroalkane and acetonitrile solvent gives a much higher conversion to a solid product and the yield of 4,4'-dithiobis(2,6-di-tert-butylphenol) is substantially improved.

I claim:

1. A process for making a 4,4'-polythiobis(2,6-dialkylphenol), said process comprising reacting a 2,6-dialkylphenol with S$_2$Cl$_2$ in a nitroalkane solvent at −10° to 30° C. to form a mixture of mainly 4,4'-dithiobis and 4,4'-trithiobis(2,6-dialkylphenol).

2. A process of claim 1 wherein said 2,6-dialkylphenol is a 2,6-di-tert-alkylphenol.

3. A process of claim 2 wherein said 2,6-di-tert-alkylphenol is 2,6-di-tert-butylphenol.

4. A process of claim 3 conducted at −10° to +15° C.

5. A process of claim 3 wherein said nitroalkane is selected from nitromethane, nitroethane, 1-nitropropane and 2nitropropane.

6. A process of claim 5 wherein said nitroalkane is nitromethane.

7. A process of claim 6 conducted at −10° to +15° C.

8. A process of claim 1 conducted in the presence of an acetonitrile co-solvent.

9. A process of claim 8 wherein said 2,6-dialkylphenol is a 2,6-di-tert-alkylphenol.

10. A process of claim 9 wherein said 2,6-di-tertalkylphenol is 2,6-di-tert-butylphenol.

11. A process of claim 10 conducted at −10° to +15° C.

12. A process of claim 10 wherein said nitroalkane is selected from nitromethane, nitroethane, 1-nitropropane and 2nitropropane and mixtures thereof.

13. A process of claim 12 wherein said nitroalkane is nitromethane.

14. The process of claim 13 conducted at −10° to +15° C.

15. A process for making a mixture of 4,4'-dithiobis and 4,4'-trithiobis(2,6-di-tert-butylphenol) said process comprising reacting one mole part of 2,6-di-tert-butylphenol with 0.45–0.55 mole parts of S$_2$Cl$_2$ at a temperature of −10° to 30° C. in a solvent comprising about 150–300 parts by weight nitromethane while removing HCl.

16. A process of claim 15 wherein said solvent comprises about 150–200 parts of nitromethane and 100–200 parts of acetonitrile.

17. A process of claim 16 wherein said solvent comprises about 180–200 parts of nitromethane and 100–130 parts by weight acetonitrile.

18. A process of claim 17 conducted at −10° to +15° C.

19. A process of claim 18 conducted at −0° to +15° C.

20. A process of claim 19 conducted while purging HCl from the reaction system with an inert gas stream.

* * * * *